United States Patent [19]

Reese et al.

[11] 4,192,858
[45] Mar. 11, 1980

[54] PRODUCTION OF RADIOIODINATED $T_3$ AND $T_4$

[75] Inventors: Max G. Reese, Salt Lake City; Richard H. Hales, West Jordan, both of Utah

[73] Assignee: Becton, Dickinson and Company, Paramus, N.J.

[21] Appl. No.: 879,800

[22] Filed: Feb. 21, 1978

[51] Int. Cl.² ......................... A61K 43/00; G21H 5/02
[52] U.S. Cl. ...................................... 424/1; 23/230 B; 23/230.3
[58] Field of Search ................ 424/1; 23/230 B, 230.3

[56] References Cited
PUBLICATIONS

Weeke et al., Scand. J. Clin. Lab. Invest., 32, 357 (1973).
Hallaba et al., J. Nucl. Med., 15, 270 (1970).
Burger et al., Endocrinology, 94, 1189 (1974).
Kjeld et al., Clin. Chem. Acta., 61, 381 (1971).
Thurlow et al., Ann. Clin. Biochem., 13, 364 (1976).
Mayberry et al., J. Biol. Chem., 245, 697 (1970).
Dobas et al., J. Chem. Soc. Perkin A, (1972), 1189.
Gleason, J. Biol. Chem., 213, 837 (1955).
Latham et al., J. Biol. Chem., 251, 7388 (1976).
Jiang et al., J. Am. Chem. Soc., 97, 6551 (1975).

Primary Examiner—Benjamin R. Padgett
Assistant Examiner—Christine M. Nucker
Attorney, Agent, or Firm—Louis E. Marn; Elliot M. Olstein

[57] ABSTRACT

The chloramine T procedure is employed to provide radioiodinated $T_3$ and radioiodinated $T_4$ from $T_3$ and $T_4$, respectively, at specified pHs and mole ratios to provide for long shelf life. $T_3$ is also radioiodinated to high specific activity radioiodinated $T_4$, and purified after a specified waiting period to remove radioactive non-antigenic contaminants and thereby provide a long shelf life.

8 Claims, No Drawings

PRODUCTION OF RADIOIODINATED T₃ AND T₄

This invention relates to the production of radioiodinated thyroxine (T$_4$) and radioiodinated triiodothyronine (T$_3$).

In the radioassay of T$_3$ and T$_4$, the most basic and variable component of the system is the tracer; i.e., the radioiodinated T$_3$ and radioiodinated T$_4$. The radioiodinated T$_3$ and radioiodinated T$_4$ should have a high immunoreactivity, purity and long shelf life. In many cases, a high specific activity is also desirable to improve sensitivity.

The present invention is directed to providing radioiodinated T$_4$ of high and medium specific activity and radioiodinated T$_3$ of medium specific activity, all of which have long term stability.

In accordance with one aspect of the present invention, triiodothyronine (T$_3$) is radioiodinated to produce radioiodinated thyroxine which after a waiting period of at least 10 days is subjected to a further purification procedure to produce radioiodinated thyroxine of high specific activity having long term stability.

In accordance with another aspect of the present invention, thyroxine is radioiodinated by the chloramine T procedure at a pH of from 5 to 10 and at a mole ratio of thyroxine to radioactive iodine of from 2:1 to 7:1 to produce radioiodinated thyroxine of medium specific activity having long term stability.

In accordance with another aspect of the present invention, triiodothryonine is radioiodinated by the chloramine T procedure at a pH of from 5 to 10 and a mole ratio of triiodothyronine to radioactive iodine of from 2:1 to 8:1 to produce radioiodinated T$_3$ of medium activity having long term stability.

The basic procedure for radioiodinating a substrate employing chloramine T as the oxidant is known in the art and the present invention employs such basic procedure. In brief, the general procedure involves combining radioactive sodium iodide; in particular, Na$^{125}$I with appropriate phosphate buffer followed by addition of the substrate (T$_3$ or T$_4$). The reaction is initiated by addition of chloramine T in buffer, with the reaction proceeding for a period of from 15 sec. to several minutes. The reaction is stopped by the addition of sodium metabisulfite.

The reaction products are then separated by adsorption chromatography; in particular, on a Sephadex column using a phosphate buffer.

The above general procedure is known in the art and no details in this respect are deemed necessary for a complete understanding of the invention.

In accordance with the aspect of the present invention for producing radioiodinated T$_4$ of high specific activity having long term stability, radioiodinated T$_4$ is prepared from T$_3$ with radioiodinated T$_4$ being recovered from the product. Applicant has found that although such a radioiodinated T$_4$ product has a high specific activity, such product is not stable (shelf life only a few weeks). Applicant has further found that it is possible to provide a radioiodinated T$_4$ product having stable antigenic properties by subjecting the product to a further purification after a waiting period of at least 10 days, preferably at least 30 days and generally a period of from 30 days to 90 days. The purification can be effected by either adsorption or ion exchange chromatography or affinity chromatography.

It is to be understood that the longer the waiting period for effecting the purification, the greater the stability of the purified product. Thus, increased stability is obtained by effecting the purification after 30 days as compared to after 10 days. Such purification is effected to remove radioactive non-antigenic contamination and the resulting purified radioiodinate T$_4$ maintains antigenicity and specific activity without further purification. Thus, it is possible to provide radioiodinated T$_4$ being a specific activity in the order of from 2000 to 3000 mCi/mg, with long term stability, in the order of at least 3 months.

The T$_3$ may be radioiodinated by any one of the wide variety of procedures known in the art, such as chloramine T procedure; Iodine monochloride method; Isotopic Exchange method; Electrolytic iodination, etc. The preferred procedure is the chloramine T procedure. In general, the radioiodination is effected at a T$_3$ to $^{125}$I mole ratio of from 1:1 to 1.5:1.

In accordance with the present invention, radioiodinated T$_4$ of medium specific activity (in the order of from 100 to 500 mCi/mg) is prepared from T$_4$ by the chloramine T procedure. The oxidation is effected at a pH of from 5 to 10, preferably from pH 8.0 to 9.0, with the T$_4$ to iodine mole ratio being from 2:1 to 6:1, and such radioiodinated T$_4$ has a medium specific activity and maintains its antigenic activity over a long period of time, generally at least 6 months. In general, the ratio of radioiodinated T$_4$ to radioiodinated T$_3$ in the product is at least 3:1 and most generally in the order of 30:1. The radioiodinated T$_3$ and T$_4$ are separated and recovered as known in the art; in particular, column chromatography.

In accordance with the present invention, radioiodinated T$_3$ of medium specific activity (in the order of from 200 to 500) mCi/mg is prepared from T$_3$ by the chloramine T procedure. The oxidation is effected at a pH of from 5 to 10, preferably from 8 to 9, with the T$_3$ to iodine mole ratio being from 2:1 to 8:1, preferably from 2.5:1 to 7:1. The radioiodinated product contains a high ratio of radioiodinated T$_3$ to radioiodinated T$_4$, and such radioiodinated T$_3$ has a medium specific activity and maintains its antigenic activity over a long period of time, generally at least 10 months. In general, the ratio of radioiodinated T$_3$ to radioiodinated T$_4$ in the product is at least 1:1 and most generally in the order of from 2:1 to 4:1. The radioiodinated T$_3$ and T$_4$ are separated and recovered as known in the art; in particular, column chromatography.

The radioiodinated T$_3$ and T$_4$; in particular $^{125}$I-T$_3$ and $^{125}$I-T$_4$, may be employed as a tracer in a radioassay for T$_3$ and T$_4$, respectively. Such radioassays are well known in the art, and no details in this respect are deemed necessary for a complete understanding of the present invention.

The invention will be further described with respect to the following examples; however the scope of the invention is not to be limited thereby

EXAMPLE I

A. A mixture of mono- and dilabeled $^{125}$I-T$_4$ is prepared by reacting $^{125}$I and T$_3$ in a molar ratio of 1:1 The mechanism of reaction is both addition and exchange and the resulting specific activity is greater than 3000 mCi/mg. The product is usable for several weeks without purification before too much of the radioactivity becomes non-antigenic.

B. 5 mCi of carrier free Na$^{125}$I, dissolved in a minimum of aqueous base (pH 8-10), is placed in a Combi-V-Vial. To this is added 20λ of a 2 μg/20λ solution of T$_3$ (free acid) dissolved in dilute ammonium hydroxide, pH 10.5. This is followed by addition of 50λ of 0.05 M phosphate buffer, pH 7.5, and then 25λ of a 90 μg/25λ solution of chloramine-T freshly dissolved in 0.05 M phosphate buffer, pH 7.5. The final pH of the mixture is 7.5. The contents of the V-Vial are mixed well and the reaction is allowed to proceed for 15 seconds whereupon 100λ of a 240 μg/100λ solution of sodium metabisulphite freshly dissolved in 0.05 M phosphate buffer, pH 7.5, is added to stop the reaction.

The products are separated by adsorption chromatography on a Sephadex G-25-80 column (1.1×14 cm). After transferring the reaction mixture to the column, it is washed with 0.05 M phosphate buffer, pH 7.5. Approximately 80 fractions of 6.0 mls each are collected and stored in dim light. Fractions 50-70 containing the $^{125}$I-T$_4$ product are combined, diluted to 50% with propylene glycol and stored in the dark at 4° C.

C. After 30 days, the $^{125}$I-T$_4$ is purified as follows: A 10λ sample of the stored $^{125}$I-T$_4$ solution is added to 0.5 ml of 0.05 M phosphate buffer, pH 7.5, mixed thoroughly, and applied to the top of a 5×20 mm Sephadex G-25-80 column. The column is washed with the same phosphate buffer and 11 fractions of approximately 2.0 mls each of the eluent are collected. The first peak, usually contained in the first fraction, consists of free iodine and is the result of the breakdown of dilabeled $^{125}$I-T$_4$. The second peak represents the remaining purified $^{125}$I-T$_4$ of much longer shelf life. The fractions containing this peak are pooled, diluted to 50% with propylene glycol and stored in the dark at 4° C.

EXAMPLE II

A. Monolabeled $^{125}$I-T$_3$ is produced by the exchange mechanism by reacting $^{125}$I and T$_3$ in a molar ratio of 1:5. The specific activity of the product is of the order of 500 mCi/mg and the radioactivity remains antigenic for more than ten months.

B. 5 mCi of carrier free Na$^{125}$I, dissolved in a minimum of aqueous base (pH 8-10), is placed in a Combi-V-Vial. To this is added 50λ of 0.05 M phosphate buffer, pH 7.5, followed by 10λ of a 10 ug/10λ solution of T (free acid) dissolved in dilute ammonium hydroxide, pH 10.5. Next is added 25λ of a 90 ug/25λ solution of chloromine-T freshly dissolved in 0.05 M phosphate buffer, pH 7.5. The final pH of the mixture is 8.6. The contents of the V-Vial are mixed well and the reaction is allowed to proceed for 15 seconds. The reaction is stopped by addition of 100λ of a 240 ug/100λ solution of sodium metabisulfite freshly dissolved in 0.05 M phosphate buffer, pH 8.7.

The products are separated by adsorption chromatography on a Sephadex G-25-80 column as in EXAMPLE I above.

EXAMPLE III

A. Monolabled $^{125}$I-T$_4$ is produced by the exchange mechanism by reacting $^{125}$I and T$_4$ in a molar ratio of 1:5. The resulting specific activity is of the order of 250 mCi/mg. This radioactive antigen is stable for greater than five months and this fact is the basis of the assumption that the $^{125}$I-T$_4$ is monolabeled.

B. 5 mCi of carrier free Na$^{125}$I, dissolved in a minimum of aqueous base (pH 8-10), is placed in a Combi-V-Vial. To this is added 50λ of 0.05 M phosphate buffer, pH 7.5, followed by 20λ of a 10 μg/20λ solution of T$_4$ (free acid) dissolved in dilute ammonium hydroxide, pH 10.5 Chloramine-T (25λ of a 90 μg/25λ solution) freshly dissolved in 0.05 M phosphate buffer, pH 7.5, is added and the solution is mixed well and allowed to react for 15 seconds. The pH of the mixture is 8.7. Sodium metabisulphite (100λ of a 240 μg/100λ solution), freshly dissolved in 0.05 M phosphate buffer, pH 7.5, is added to stop the reaction and the products are separated by adsorption chromatography on Sephadex G-25-80 as described in EXAMPLE I above.

Numerous modifications and variations of the present invention are possible in light of the above teachings and, therefore, within the scope of the appended claims the invention may be practiced otherwise than as particularly described.

We claim:

1. In a process for producing radioiodinated T$_4$ of high specific activity by radioiodination of T$_3$, the improvement comprising:
    after a period of at least 10 days further purifying said radioiodinated T$_4$ to remove radioactive non-antigenic contamination and provide radioiodinated T$_4$ of high specific activity having long term stability.

2. The process of claim 1 wherein the radioiodinated T$_4$ has a specific activity of from 2000 to 3000 m Ci/mg.

3. The process of claim 2 wherein the radioiodination is effected by the chloramine T procedure.

4. The process of claim 3 wherein said period is at least 30 days.

5. The process of claim 4 wherein the radioiodine is $^{125}$I.

6. The process of claim 2 wherein said purification is effected by ion exchange chromatography.

7. The process of claim 2 wherein said purification is effected by absorption chromatography.

8. The process of claim 2 wherein said purification is effected by affinity chromatography.

* * * * *